US011672998B2

(12) United States Patent
Compton et al.

(10) Patent No.: US 11,672,998 B2
(45) Date of Patent: *Jun. 13, 2023

(54) ENCASED MAGNETIC BONE GROWTH STIMULATING DEVICES AND METHODS OF USE

(71) Applicants: Robert A Compton, Bixby, OK (US); Nicholas Michael Cordaro, Vista, CA (US); Robert Alex Hirschl, Lake Huges, IA (US)

(72) Inventors: Robert A Compton, Bixby, OK (US); Nicholas Michael Cordaro, Vista, CA (US); Robert Alex Hirschl, Lake Huges, IA (US)

( * ) Notice: Subject to any disclaimer, the term of this patent is extended or adjusted under 35 U.S.C. 154(b) by 170 days.

This patent is subject to a terminal disclaimer.

(21) Appl. No.: 17/023,472

(22) Filed: Sep. 17, 2020

(65) Prior Publication Data

US 2021/0170187 A1 Jun. 10, 2021

Related U.S. Application Data

(63) Continuation of application No. 15/799,525, filed on Oct. 31, 2017, now Pat. No. 10,780,290.

(60) Provisional application No. 62/416,041, filed on Nov. 1, 2016.

(51) Int. Cl.
*A61N 2/00* (2006.01)
*A61B 17/70* (2006.01)
*A61N 2/06* (2006.01)

(52) U.S. Cl.
CPC .......... *A61N 2/004* (2013.01); *A61B 17/7049* (2013.01); *A61N 2/06* (2013.01); *A61B 17/7032* (2013.01)

(58) Field of Classification Search
CPC ............ A61N 2/00–12; A61B 17/7032; A61B 17/7049
See application file for complete search history.

(56) References Cited

U.S. PATENT DOCUMENTS

| 9,339,309 | B1* | 5/2016 | Geist | A61B 17/7083 |
|---|---|---|---|---|
| 2004/0059423 | A1* | 3/2004 | Barnes | A61N 2/06 600/12 |
| 2007/0179493 | A1* | 8/2007 | Kim | A61F 2/442 606/33 |
| 2012/0035661 | A1* | 2/2012 | Pool | A61B 17/7004 606/258 |
| 2013/0006356 | A1* | 1/2013 | Cook | A61F 2/78 623/16.11 |
| 2014/0296919 | A1* | 10/2014 | Culbert | A61B 17/863 606/272 |
| 2015/0105826 | A1* | 4/2015 | Green | A61B 17/707 606/279 |
| 2015/0251014 | A1* | 9/2015 | Hirschl | A61N 2/002 600/12 |

* cited by examiner

*Primary Examiner* — Thaddeus B Cox
(74) *Attorney, Agent, or Firm* — David Meibos; Maywood IP Law

(57) ABSTRACT

Encased magnetic bone growth stimulating devices and methods of use are provided herein. An example device includes a magnet and a biocompatible means for enclosing the magnet. The biocompatible means for enclosing the magnet further comprises a means for releasably coupling with the medical implant and a means for coupling the enclosing means to an implantable medical device.

13 Claims, 9 Drawing Sheets

ENCASED MAGNETIC BONE GROWTH STIMULATING DEVICES AND METHODS OF USE

CROSS REFERENCE TO RELATED APPLICATIONS

This application is a continuation of and claims the benefit and priority of U.S. patent application Ser. No. 15/799,525, filed on Oct. 31, 2017, which issued as U.S. Pat. No. 10,780,290 on Sep. 22, 2020, which claims the benefit and priority of U.S. Provisional Application Ser. No. 62/416,041, filed on Nov. 1, 2016, each of which is hereby incorporated by reference herein in its entirety, including all references and appendices cited therein, for all purposes.

FIELD OF THE INVENTION

The present technology pertains to devices and methods for encased magnets for use in bone growth stimulation, and more particularly, but not by way of limitation, to rare-earth magnets in a biocompatible encasement such as a canister or screw.

SUMMARY

Various embodiments of the present disclosure are directed to a device, comprising: an enclosure comprising: a first portion having: a tubular sidewall that is enclosed on a second end thereof to form an enclosure cavity; and a second portion that is a cap that is capable of creating a hermetic seal when joined to a first end of the first portion; and a rare-earth magnet disposed within the enclosure cavity.

Various embodiments of the present disclosure are directed to a method, comprising: installing one or more rods proximate a spine of a patient; and coupling a device to at least one of the one or more rods, the device comprising: a body portion having a body portion cavity that receives a rare-earth magnet that is hermetically sealed inside the body portion cavity; the rare-earth magnet disposed inside the body portion cavity; and a coupling hook extending from the body portion; wherein coupling further comprises overlapping at least one of the one or more rods with the coupling hook. The rare earth magnet may be in a fixed location within the cavity or the cavity may be slightly enlarged so that the rare earth magnet is free to translate and or pivot with the cavity.

Various embodiments of the present disclosure are directed to a device, comprising: an implantable medical device; a magnet; and a biocompatible means for enclosing the magnet, wherein biocompatible means for enclosing the magnet further comprises a means for releasably coupling with the implantable medical device.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

Generally described, the present technology is directed to encased magnets, medical devices comprising these encased magnets, and medical treatment methods using the same. In some embodiments, a rare earth magnet is encased in a biocompatible material so as to allow for the magnet to be implanted in a body of a patient. For example, the rare earth magnet can be encased in a metal or alloy. The encased magnet can be placed near an area of treatment within a patient, such as a bone. The magnet can be utilized to, for example, stimulate bone growth.

Figure 1:
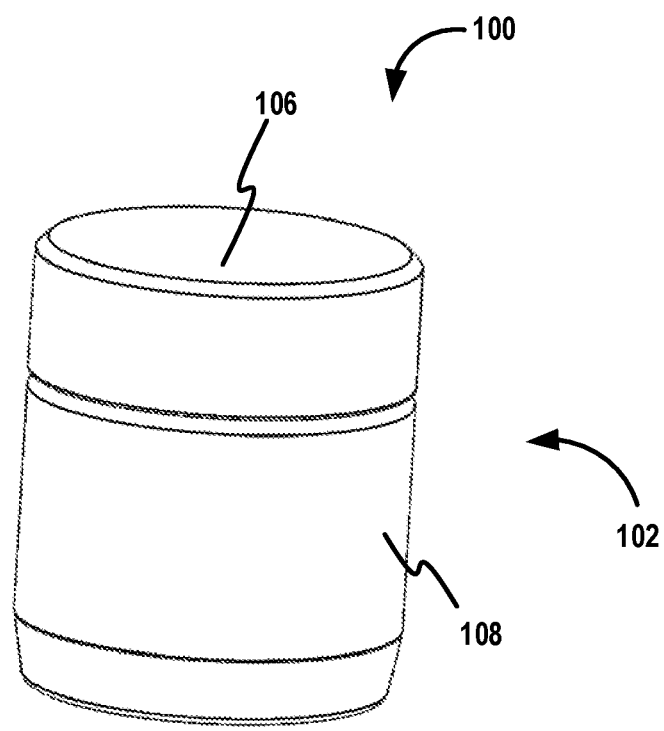
FIG. 1 is a perspective view of an encased magnet device constructed in accordance with the present disclosure.
Figure 2:
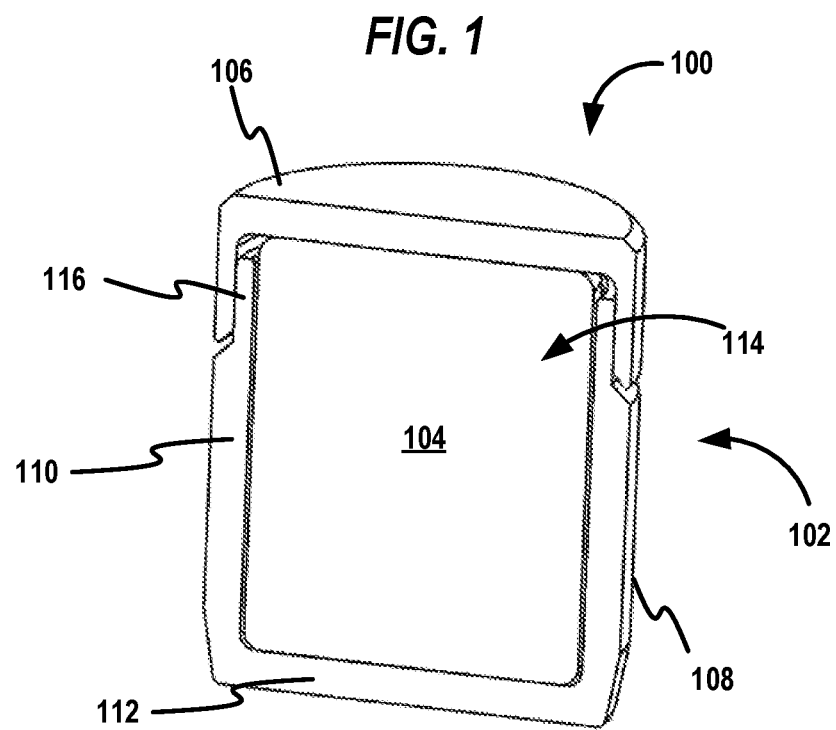
FIG. 2 is a cross-sectional view of the encased magnet device of FIG. 1.

Referring now to FIGS. 1 and 2 which collectively illustrate an example encased magnet device 100. In some embodiments, the device 100 generally comprises an enclosure 102 (e.g., a two part canister) and magnet 104. In some embodiments, the enclosure 102 is manufactured from a biocompatible material selected from pure titanium, titanium alloy, polyetheretherketone or other similar material that generally is capable of being disposed inside a human body. The selected material should be capable of withstanding degradation when implanted into a patient.

In various embodiments, the enclosure 102 comprises a first portion 106 and a second portion 108. In more detail, the first portion comprises a tubular sidewall 110 that is enclosed on a second end 112 thereof. The tubular sidewall 110 and second end 112 form an enclosure cavity 114. While the enclosure 102 is illustrated as a generally canister shaped device, the enclosure can take any desired geometrical configuration. Also, the enclosure cavity 114 can be configured to receive a magnet of any shape or size.

In some embodiments, the second portion 108 is a cap that completes the enclosure 102 by covering an open end of the first portion 106. In some embodiments, the second portion 108 can be line-to-line or press fit with the first portion 106 and then sealed by any means that is compatible with the material such as laser welding, sonic welding, or other similar means.

In one or more embodiments, the first end of the first portion 106 comprises a flange 116 that mates with the second portion 106 of the enclosure 102. The flange 116 is created by a tapering of sidewall 110.

In some embodiments, the device 100 may be inserted into or onto varying implantable medical device embodiments by means of a press fit, snap fit, or other means such as threading or welding, as will be discussed in greater detail infra.

In various embodiments, the first portion 106 and the second portion 108 are hermetically sealed to one another when joined together. This hermetic sealing could be effectuated using the examples provided above or using, for example, an adhesive at the interface between the first portion 106 and the second portion 108.

In some embodiment, the magnet 104 may include any type of magnet that is desired for a particular medical treatment such as stimulating bone growth. In various embodiments, the magnet 104 comprises a rare-earth magnet that is selected from any of neodymium comprised of at least some portion of Neodymium (Nd), Iron (Fe) and Boron (B), any combinations thereof, along with other magnets that would be known to one of skill in the art.

Figure 3:
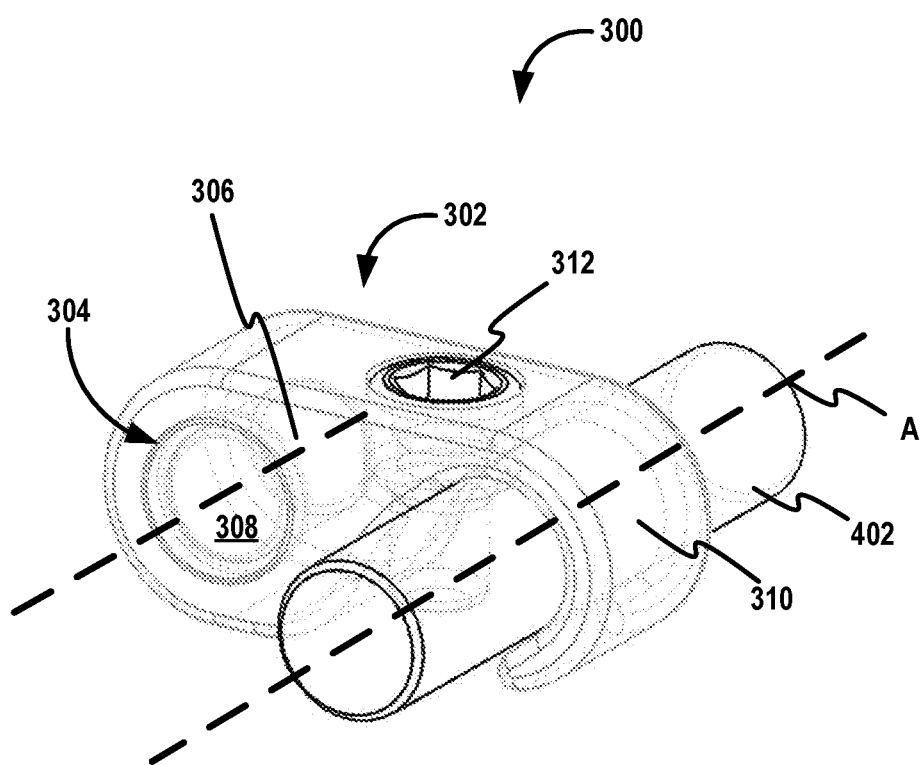
FIG. 3 is a perspective view of an example implantable medical device, constructed in accordance with the present disclosure.

FIG. 3 illustrates an example a rod coupling assembly 300. The rod coupling assembly 300 generally comprises a body portion 302 having a body portion cavity 304 that receives the enclosure having the rare-earth magnet 306.

The body portion 302 can comprise a cap or cover plate 308 that covers an open end of the body portion cavity 304. The assembly 300 can be manufactured from any of the biocompatible materials described above.

In some embodiments, the rare-earth magnet 306 hermetically sealed inside the body portion cavity 304 by placing the rare-earth magnet 306 therein and then sealing the body portion cavity 304 with the cover plate 308. Again, this can include laser welding, compressive fitting, sonic welding, adhesives, and/or any other similar methods.

In another embodiment, a device, such as the device 100 of FIG. 1 can be inserted into the body portion cavity 304. In these embodiments, the cover 308 may or may not be utilized.

Figure 4:
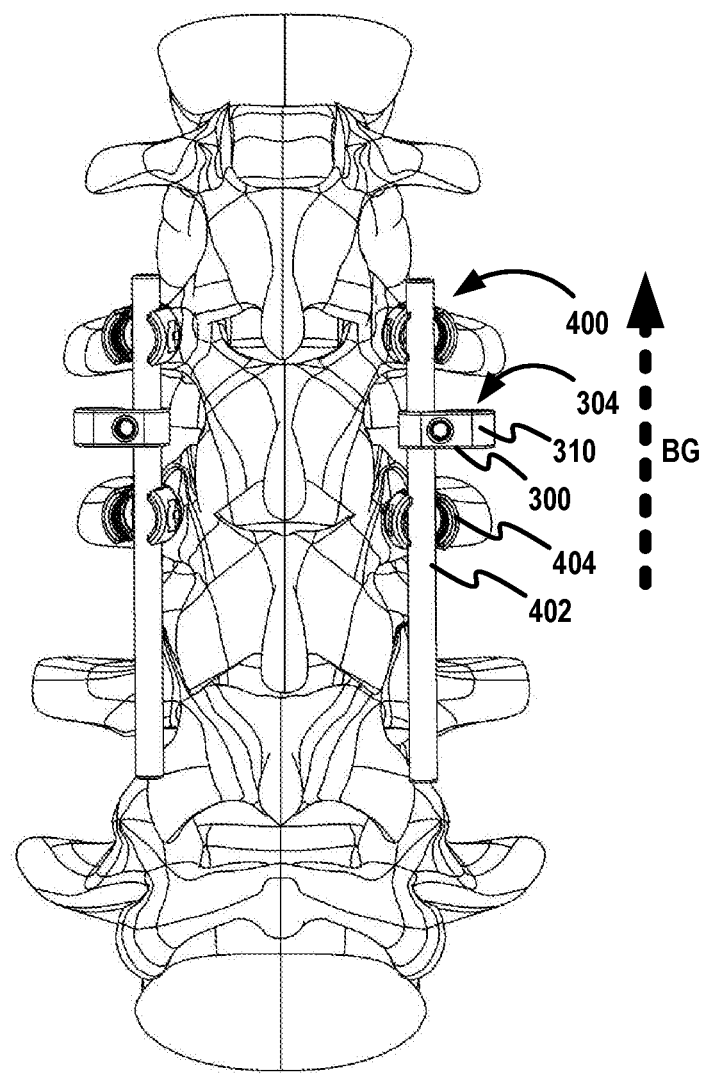
FIG. 4 is a front facing perspective view of the example implantable medical device installed on a rod of a spinal implant.
Figure 5:
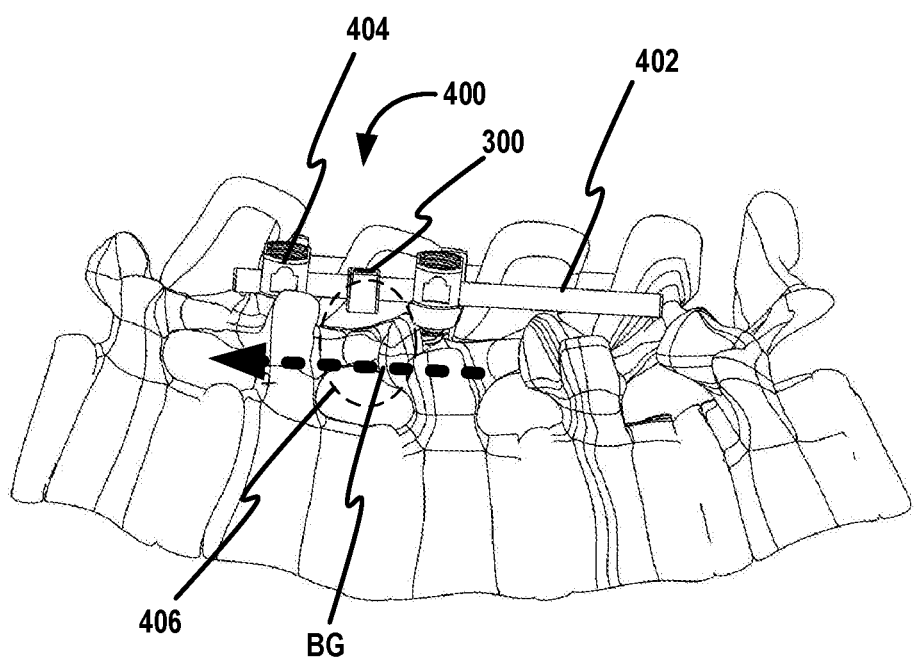
FIG. 5 is a side facing perspective view of the example implantable medical device installed on a rod of a spinal implant construct.

According to some embodiments, the assembly 300 comprises a coupling hook 310 that releasably attaches to a rod of a spinal implant, as illustrated in FIGS. 4 and 5, and discussed in greater detail below.

In accordance with the present disclosure, the body portion 302 further comprises a locking member 312 disposed between the body portion cavity 304 and the coupling hook 310. The locking member 312 is inserted into an aperture formed in a linkage between the body portion 302 and the coupling hook 310. The locking member 312 prevents removal of the rod coupling assembly 300 from a rod of a spinal implant construct when the locking member 312 is installed.

In FIGS. 4 and 5, an implantable medical device 400 is illustrated that includes at least one spinal rod 402 that are coupled to posts or fixation screws, such as post or fixation screw 404. The assembly 300 of FIG. 3 is attached lateral or medial along the spinal rod 402 to produce a static magnet field along the posterior lateral fusion site 406 (see FIG. 5), or other clinically appropriate fusion site located in proximity to the lateral or medial edge of the spinal rod 402. In sum, the body portion cavity 304 is oriented in such a way that the rare-earth magnet 306 (either inside the cavity or inside an enclosure placed in the cavity) has at least one magnetic pole end 314 (see FIG. 3) that is oriented in a direction of desired bone growth denoted by arrow BG. In sum a direction or directions of bone growth is/are dictated by orientation of the poles of the magnet(s) in the assembly 300.

In some embodiments, as illustrated in FIG. 3, the body portion cavity 304 is oriented in parallel with a central axis A of the spinal rod 402. In another embodiment, the body portion cavity can be oriented perpendicular to the central axis A.

In operation, the implantable medical device 400 is installed onto the spine of the patient. The assembly 300 is installed on the spinal rod 402 by engaging the coupling hook 310 with the spinal rod 402. Next, to secure the assembly 300, the locking member 312 is inserted into the assembly 300.

After the assembly 300 is installed, it can remain within the patient for a period of time and then be removed at a later date. Thus, the assembly 300 can be removed by removing the locking member 312 and decoupling the coupling hook 310 from the spinal rod 402.

To be sure, the locking member 312 is not required and some embodiments may allow for the coupling hook 310 to be crimped onto the spinal rod 402 with a tool.

Figure 6:
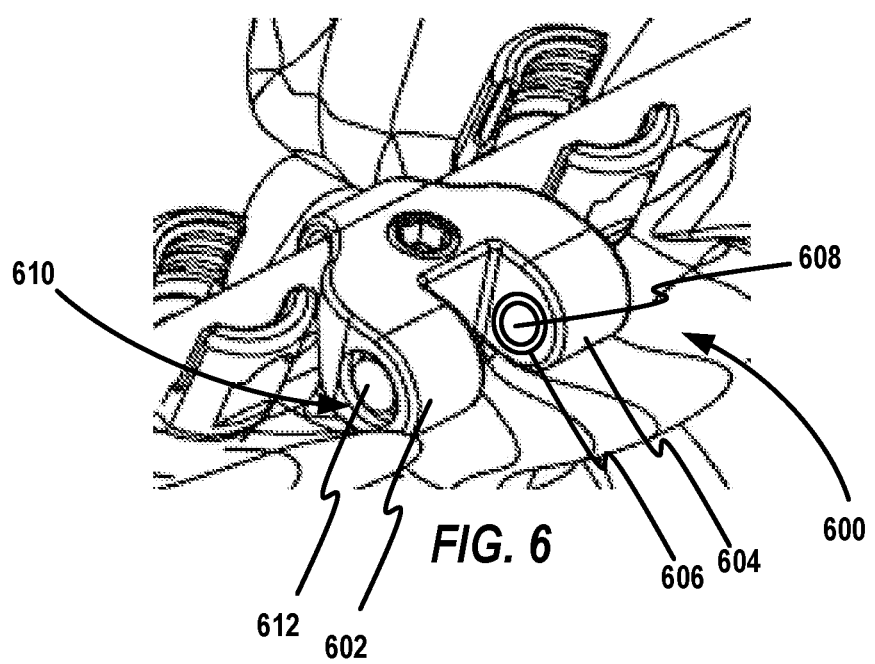
FIG. 6 is a perspective view of another example implantable medical device installed on a rod of a spinal implant construct.

FIG. 6 illustrates another example embodiment of a rod coupling assembly 600. This embodiment is similar in construction to the rod coupling assembly 300 of FIGS. 3-5, with the exception that the rod coupling assembly 600 comprises a first body portion 602 and a second body portion 604. The first portion 602 has a first body portion cavity 610 with a first magnet 612 disposed therein. The second body portion cavity 606 of the second body portion 604 receives a second rare-earth magnet 608. Thus, the assembly 600 can comprise a coupling hook and/or a locking member, as well for installation and securement to a spinal rod of a spinal implant.

Figure 7:
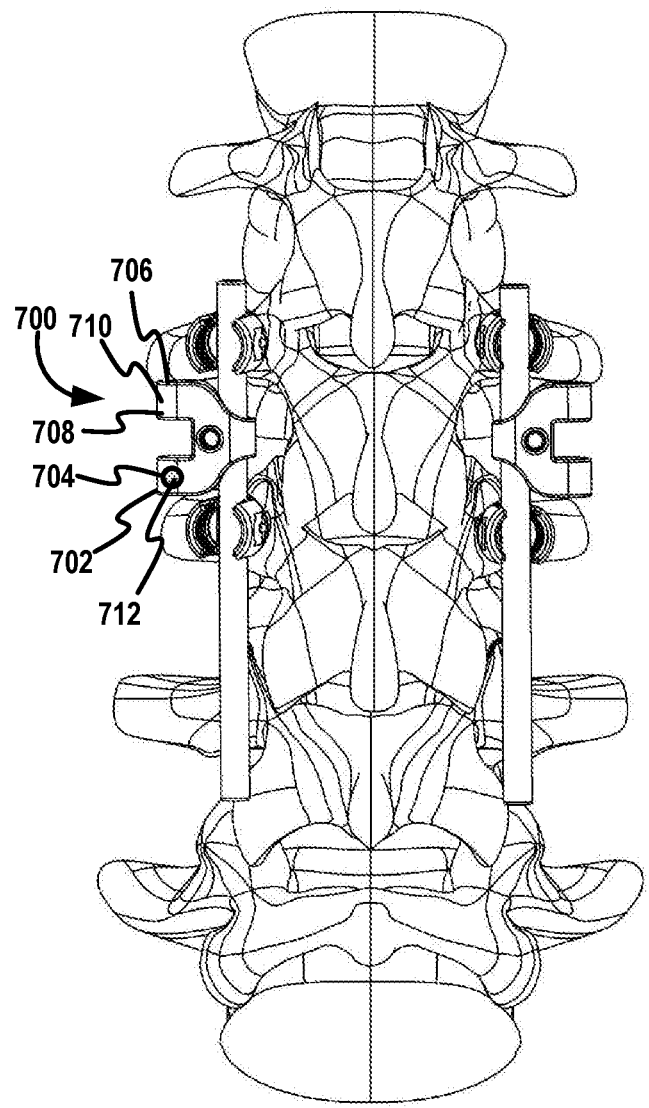
FIG. 7 is a front facing perspective view of the example implantable medical device of FIG. 6, installed on a rod of a spinal implant construct.
Figure 8:
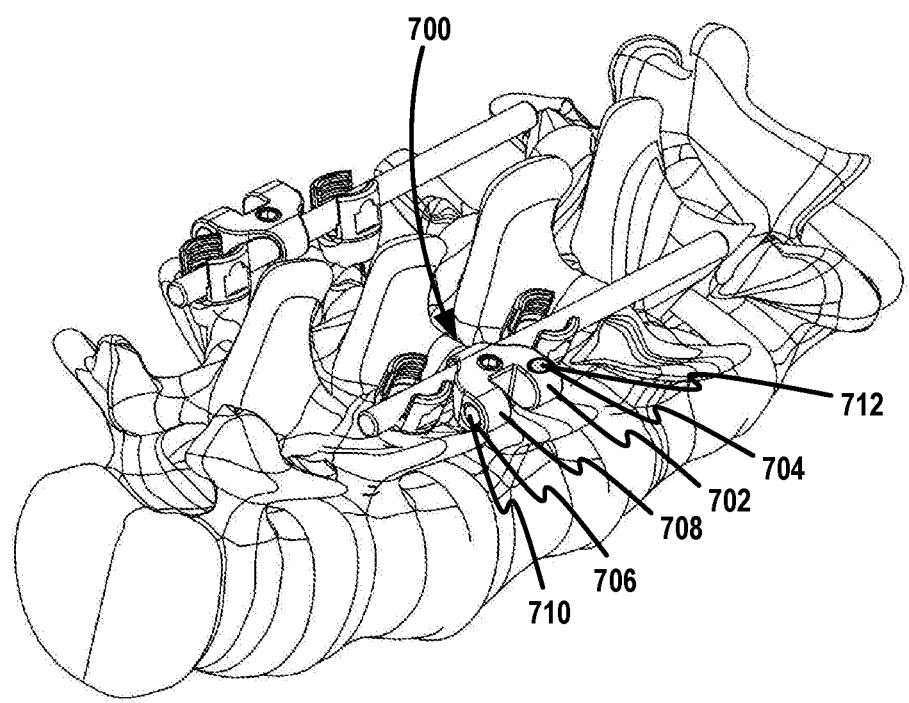
FIG. 8 is a perspective view of the example implantable medical device of FIGS. 6-7 installed on a rod of a spinal implant construct.

As illustrated in FIGS. 7 and 8, another rod coupling assembly 700 includes a second body portion 702 having a second body portion cavity 704 oriented in a direction that is opposite of the body portion cavity 706 of a first body portion 708 such that a pole of a magnet 710 (can be rare-earth) in the first body portion 708 and a pole of the second magnet 712 (can be rare-earth) are oriented in different directions relative to one another (in this instance orthogonal). This allows for bone growth stimulation in two planes. Additional body portions can be added as desired.

Figure 9:
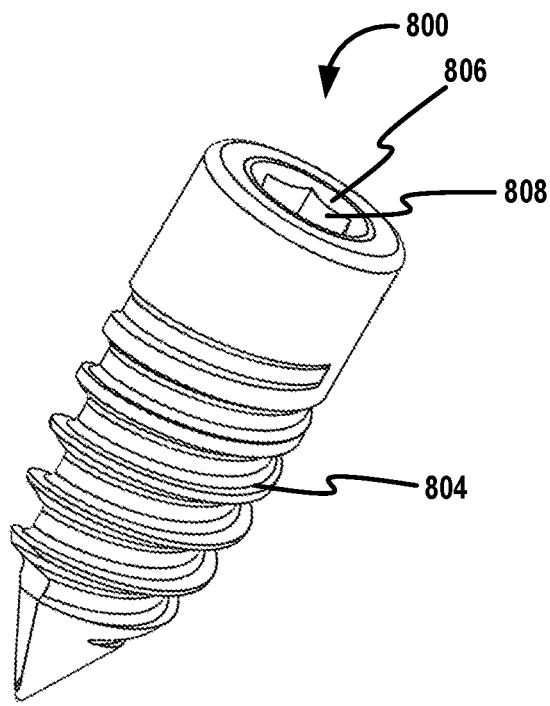
FIG. 9 is a perspective view of another example encased magnet device in the form of a screw that is constructed in accordance with the present disclosure.
Figure 10:
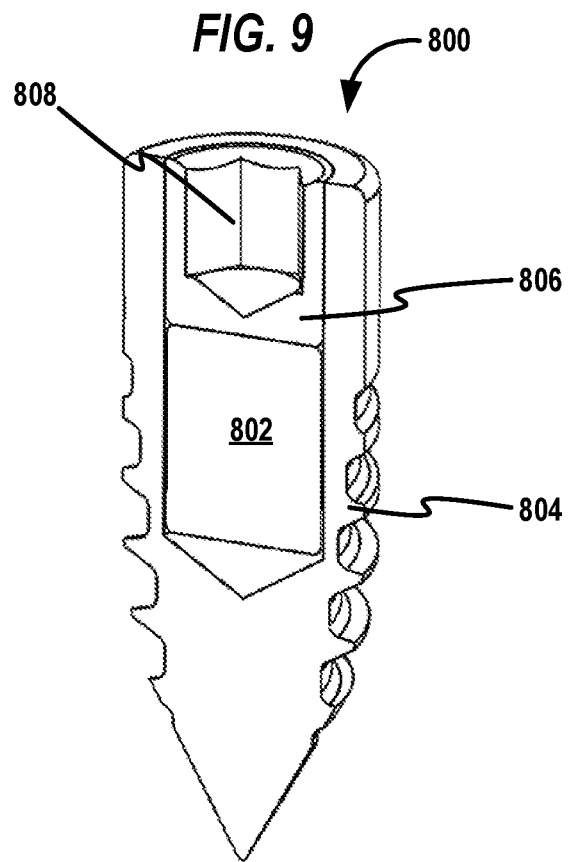
FIG. 10 cross-sectional view of the encased magnet device of FIG. 9.

FIGS. 9 and 10 collectively illustrate another example enclosed magnet device 800. In this embodiment, a magnet 802 can be hermetically sealed within a biocompatible threaded screw body 804 made from, for example, commercially pure titanium, titanium alloy, polyetheretherketone or other similar material. The biocompatible threaded screw body 804 of the device 800 is a first portion of the device 800 and a plug or screw lid 806 functions as a second portion of the enclosure. The plug or screw lid 806 includes a tool interface 808 for receiving an end of a tool In some embodiments, the screw lid 806 is secured to the biocompatible threaded screw body 804 using line-to-line or press fit. These two portions are then sealed by any sealing means compatible with the material such as laser welding, sonic welding, or other means. All or a portion of the enclosure may be produced by additive manufacturing. The additive manufacturing process may be paused, the magnet introduced into the enclosure, then the additive manufacturing process restarted. This will allow the magnet to be fully sealed. An example additive manufacturing process that can be utilized in accordance with the present disclosure can be found in co-pending application Ser. No. 15/488,449, which is hereby incorporated by reference herein in its entirety, including all references and appendices cited therein.

The screw could be used by itself or to retain a plate or other rigid or flexible bone fixation member.

The enclosed magnet device 800 may be placed into an available thru hole on a bone fracture plate or threaded directly along a new or non-union bone fracture, or in other surgical locations where bone fusion is desired.

Figure 11:
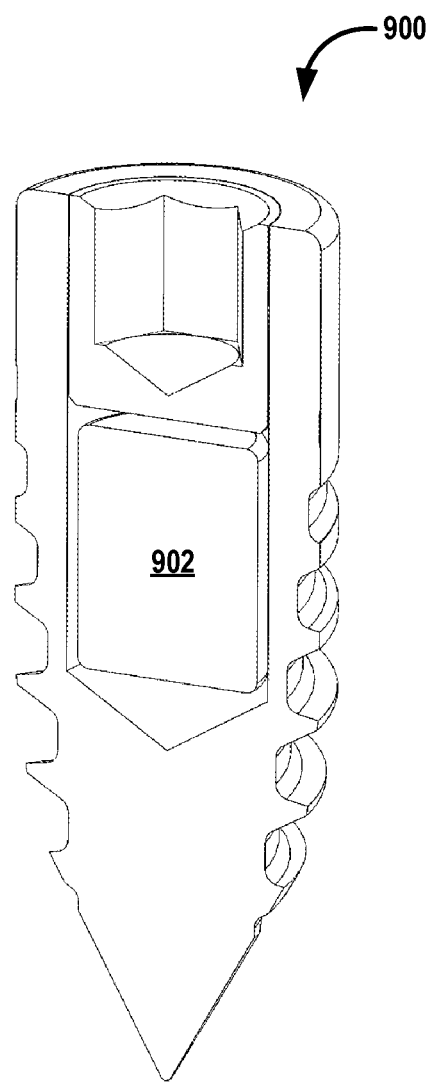
FIG. 11 cross-sectional view of another enchased magnet device allowing for internal movement of the magnet.

The magnet within the enclosure is restricted in size to reduce the distance from the magnet to the surrounding anatomy. This will maximize the resultant magnetic field around the device. In some instances, as shown in FIG. 11, a magnet 902 will be free to pivot and or translate within an enclosure 900, such as a screw. This will produce a slightly isolating static magnetic field resulting from patient movement. The magnet will move due to gravitational and inertia forces as enclosure moves while the patient changes positions.

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the present technology in the form disclosed. Many modifications and variations will be apparent to those of ordinary skill in the art without departing from the scope and spirit of the present technology. Exemplary embodiments were chosen and described in order to best explain the principles of the present technology and its practical application, and to enable others of ordinary skill in the art to understand the present technology for various embodiments with various modifications as are suited to the particular use contemplated.

Aspects of the present technology are described above with reference to flowchart illustrations and/or block diagrams of methods, apparatus (systems) and computer program products according to embodiments of the present technology. It will be understood that each block of the flowchart illustrations and/or block diagrams, and combinations of blocks in the flowchart illustrations and/or block diagrams, can be implemented by computer program instructions.

In the following description, for purposes of explanation and not limitation, specific details are set forth, such as particular embodiments, procedures, techniques, etc. in order to provide a thorough understanding of the present invention. However, it will be apparent to one skilled in the art that the present invention may be practiced in other embodiments that depart from these specific details.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

Also, some embodiments may be described in terms of "means for" performing a task or set of tasks. It will be understood that a "means for" may be expressed herein in terms of a structure, such as a processor, a memory, an I/O device such as a camera, or combinations thereof. Alternatively, the "means for" may include an algorithm that is descriptive of a function or method step, while in yet other embodiments the "means for" is expressed in terms of a mathematical formula, prose, or as a flow chart or signal diagram.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It is noted at the outset that the terms "coupled," "connected", "connecting," "electrically connected," etc., are used interchangeably herein to generally refer to the condition of being electrically/electronically connected. Similarly, a first entity is considered to be in "communication" with a second entity (or entities) when the first entity electrically sends and/or receives (whether through wireline or wireless means) information signals (whether containing data information or non-data/control information) to the second entity regardless of the type (analog or digital) of those signals. It is further noted that various figures (including component diagrams) shown and discussed herein are for illustrative purpose only, and are not drawn to scale.

If any disclosures are incorporated herein by reference and such incorporated disclosures conflict in part and/or in whole with the present disclosure, then to the extent of conflict, and/or broader disclosure, and/or broader definition of terms, the present disclosure controls. If such incorporated disclosures conflict in part and/or in whole with one another, then to the extent of conflict, the later-dated disclosure controls.

The terminology used herein can imply direct or indirect, full or partial, temporary or permanent, immediate or delayed, synchronous or asynchronous, action or inaction. For example, when an element is referred to as being "on," "connected" or "coupled" to another element, then the element can be directly on, connected or coupled to the other element and/or intervening elements may be present, including indirect and/or direct variants. In contrast, when an element is referred to as being "directly connected" or "directly coupled" to another element, there are no intervening elements present.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be necessarily limiting of the disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence or addition of one or more other features, integers, steps, operations, elements, components, and/or groups thereof.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing and/or other any other types of manufacturing. For example, some manufacturing processes include three dimensional (3D) printing, laser cutting, computer numerical control (CNC) routing, milling, pressing, stamping, vacuum forming, hydroforming, injection molding, lithography and/or others.

Any and/or all elements, as disclosed herein, can include, whether partially and/or fully, a solid, including a metal, a mineral, a ceramic, an amorphous solid, such as glass, a glass ceramic, an organic solid, such as wood and/or a polymer, such as rubber, a composite material, a semiconductor, a nano-material, a biomaterial and/or any combinations thereof. Any and/or all elements, as disclosed herein, can include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, non-transparency, luminescence, anti-reflection and/or holographic, a photo-sensitive coating, an electronic and/or thermal property coating, such as for passivity, insulation, resistance or conduction, a magnetic coating, a water-resistant and/or waterproof coating, a scent coating and/or any combinations thereof.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

Furthermore, relative terms such as "below," "lower," "above," and "upper" may be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings is turned over, then the elements described as being on the "lower" side of other elements would then be oriented on "upper" sides of the other elements. Similarly, if the device in one of the figures is turned over, elements described as "below" or "beneath" other elements would then be oriented "above" the other elements. Therefore, the example terms "below" and "lower" can, therefore, encompass both an orientation of above and below.

While various embodiments have been described above, it should be understood that they have been presented by way of example only, and not limitation. The descriptions are not intended to limit the scope of the invention to the particular forms set forth herein. To the contrary, the present descriptions are intended to cover such alternatives, modifications, and equivalents as may be included within the spirit and scope of the invention as defined by the appended claims and otherwise appreciated by one of ordinary skill in the art. Thus, the breadth and scope of a preferred embodiment should not be limited by any of the above-described exemplary embodiments.

What is claimed is:

1. A device, comprising:
a magnet; and
a rod coupling assembly comprising:
   a body portion having a body portion cavity that receives the magnet; and
   a coupling hook that attaches to a spinal implant construct.

2. The device according to claim 1, further comprising a first portion having an enclosure cavity that receives the magnet, and a second portion that is a cap joined to the first portion, wherein the body portion cavity further receives the first portion containing the magnet and the first portion comprises a flange that mates with the second portion.

3. The device according to claim 2, wherein the first portion is threaded to create a screw having a pointed tip and the second portion comprises a plug that seals the first portion, the plug being a tool interface.

4. The device according to claim 1, wherein the body portion further comprises a cover plate that seals the body portion cavity.

5. The device according to claim 1, wherein the body portion further comprises a locking member disposed between the body portion cavity and the coupling hook, the locking member preventing removal of the rod coupling assembly from the spinal implant construct when the locking member is installed.

6. The device according to claim 1, wherein the spinal implant construct comprises a rod and the body portion cavity is oriented in parallel with a central axis of the rod.

7. The device according to claim 1, wherein the body portion cavity is oriented in such a way that the magnet has at least one magnetic pole that is oriented in a direction of desired bone growth.

8. The device according to claim 1, wherein the rod coupling assembly further comprises a second body portion having a second body portion cavity that receives a second magnet, wherein the second body portion cavity is oriented in a direction that is opposite of the body portion cavity such that poles of the magnet and the second magnet are oriented in different directions relative to one another.

9. A device, comprising:
   an implantable medical device; and
   a magnet in a biocompatible enclosure comprising a hook for releasably coupling with the implantable medical device.

10. The device according to claim 9, wherein the implantable medical device comprises a surgical rod that is implantable in a patient.

11. The device according to claim 9, wherein the biocompatible enclosure comprises a screw.

12. The device according to claim 9, wherein the biocompatible enclosure comprises a two part canister, the two part canister comprising a hermetic seal that protects contents inside the two part canister.

13. The device according to claim 9, wherein the biocompatible enclosure allows for movement of the magnet due to gravitational and inertia forces as the biocompatible enclosure moves.

* * * * *